(12) United States Patent
Carpentier et al.

(10) Patent No.: US 10,085,836 B2
(45) Date of Patent: *Oct. 2, 2018

(54) PROSTHETIC MITRAL VALVE (71) Applicant: Edwards Lifesciences Corporation, Irvine, CA (US)

(72) Inventors: Alain F. Carpentier, Paris (FR); Hung L. Lam, Norco, CA (US); Hugues Lafrance, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/674,203

(22) Filed: Aug. 10, 2017

(65) Prior Publication Data

US 2017/0333188 A1    Nov. 23, 2017

Related U.S. Application Data (63) Continuation of application No. 14/881,061, filed on Oct. 12, 2015, now Pat. No. 9,730,794, which is a continuation of application No. 14/256,763, filed on Apr. 18, 2014, now Pat. No. 9,155,617, which is a continuation of application No. 13/229,346, filed on Sep. 9, 2011, now Pat. No. 8,721,716, which is a continuation of application No. 12/889,223, filed on
(Continued)

(51) Int. Cl.
*A61F 2/24* (2006.01)

(52) U.S. Cl.
CPC .............. *A61F 2/2448* (2013.01); *A61F 2/24* (2013.01); *A61F 2/2403* (2013.01); *A61F 2/2409* (2013.01); *A61F 2/2412* (2013.01); *A61F 2/2418* (2013.01); *A61F 2230/0008* (2013.01); *A61F 2230/0069* (2013.01); *A61F 2230/0076* (2013.01); *A61F 2230/0095* (2013.01)

(58) Field of Classification Search
CPC ........ A61F 2/24; A61F 2/2409; A61F 2/2412; A61F 2/2418
See application file for complete search history.

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0084395 A1 | 7/1983 |
| EP | 0125393 A1 | 11/1984 |

(Continued)

*Primary Examiner* — Christopher D Prone
*Assistant Examiner* — Suba Ganesan
(74) *Attorney, Agent, or Firm* — Pui Tong Ho (57) ABSTRACT

A prosthetic mitral valve with a compressible and expandable stent that, when expanded, is circumferentially oval, elliptical, or D-shaped, with a major axis and a minor axis ratio of from about 3:4 to about 4:5. Embodiments of the stent comprise three commissure regions disposed towards an outflow end and three curved cusp regions between adjacent commissure regions. Three flexible leaflets are attached to the commissure regions in a tri-foil configuration. Embodiments of the prosthetic mitral valve include an atrial ring disposed at the inflow end of the stent.

18 Claims, 7 Drawing Sheets

Related U.S. Application Data

Sep. 23, 2010, now Pat. No. 8,034,104, which is a continuation of application No. 11/039,522, filed on Jan. 19, 2005, now Pat. No. 7,871,435.

(60) Provisional application No. 60/538,516, filed on Jan. 23, 2004.

(56) References Cited

U.S. PATENT DOCUMENTS

| | | | |
|---|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,086,612 A | 7/2000 | Jansen |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |

(56) References Cited

U.S. PATENT DOCUMENTS

| | | |
|---|---|---|
| 6,440,164 B1 | 8/2002 | Di Matteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,998,151 B2 | 8/2011 | St. Goar et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109921 A1 | 6/2003 | Moe et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1* | 9/2003 | Lane .................. A61F 2/2412 623/2.14 |
| 2003/0236568 A1 | 12/2003 | Hojeibane et al. |
| 2004/0006384 A1 | 1/2004 | McCarthy |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |

(56) References Cited

U.S. PATENT DOCUMENTS

| | | |
|---|---|---|
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192599 A1 | 7/2009 | Lane et al. |
| 2010/0049313 A1 | 2/2010 | Alon et al. |

FOREIGN PATENT DOCUMENTS

| | | |
|---|---|---|
| EP | 0143246 A2 | 6/1985 |
| SU | 1116573 A1 | 7/1985 |
| SU | 1697790 A1 | 12/1991 |
| WO | 8300617 A1 | 3/1983 |
| WO | 9213502 A1 | 8/1992 |
| WO | 9742871 A1 | 11/1997 |

* cited by examiner

PROSTHETIC MITRAL VALVE

CROSS REFERENCE TO RELATED APPLICATIONS

The application is a continuation of U.S. patent application Ser. No. 14/881,061, filed Oct. 12, 2015, now U.S. Pat. No. 9,730,794, which is a continuation of U.S. patent application Ser. No. 14/256,763, filed Apr. 18, 2014, now U.S. Pat. No. 9,155,617, which is a continuation of U.S. patent application Ser. No. 13/229,346, filed Sep. 9, 2001, now U.S. Pat. No. 8,721,716, which is a continuation of U.S. patent application Ser. No. 12/889,223, filed Sep. 23, 2010, now U.S. Pat. No. 8,034,104, which is a continuation of U.S. patent application Ser. No. 11/039,522, filed Jan. 19, 2005, now U.S. Pat. No. 7,871,435, which claims the benefit of U.S. Patent Application No. 60/538,516, filed Jan. 23, 2004, the entire disclosures of which are incorporated by reference herein.

FIELD OF THE INVENTION

The present invention relates generally to medical devices, and more particularly to a prosthetic mitral heart valve having an asymmetric periphery and unequal leaflets.

BACKGROUND OF THE INVENTION

Two primary types of heart valve replacements or prostheses are known. One is a mechanical-type heart valve that uses a ball and cage arrangement or a pivoting mechanical closure supported by a base structure to provide unidirectional blood flow, such as shown in U.S. Pat. No. 4,306,319 to Kaster. The other is a tissue-type or "bioprosthetic" valve having flexible leaflets supported by a base structure and projecting into the flow stream that function much like those of a natural human heart valve and imitate their natural action to coapt against each other and ensure one-way blood flow.

In tissue-type valves, a whole xenograft valve (e.g., porcine) or a plurality of xenograft leaflets (e.g., bovine pericardium) typically provide fluid occluding surfaces. Synthetic leaflets have been proposed, and thus the term "flexible leaflet valve" refers to both natural and artificial "tissue-type" valves. Two or more flexible leaflets are mounted within a peripheral support structure that usually includes posts or commissures extending in the outflow direction to mimic natural fibrous commissures in the native annulus. Components of the valve are usually assembled with one or more biocompatible fabric (e.g., Dacron) coverings, and a fabric-covered sewing ring is provided on the inflow end of the peripheral support structure.

In most bioprosthetic-type valves, metallic or polymeric structure provides base support for the flexible leaflets, which extend therefrom. One such support is an elastic "support frame," sometimes called a "wireform" or "stent," which has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. The support frame typically describes a conical tube with the commissure tips at the small diameter end. This provides an undulating reference shape to which a fixed edge of each leaflet attaches (via components such as fabric and sutures) much like the natural fibrous skeleton in the aortic annulus. One example of the construction of a flexible leaflet valve is seen in U.S. Pat. No. 5,928,281 to Huynh, et al. (Edwards Lifesciences, Corp., Irvine, Calif.), in which the exploded view of FIG. 1 illustrates a fabric-covered wireform 54 and a fabric-covered support stent 56 on either side of a leaflet subassembly 52.

Many other flexible leaflet valve configurations are known, including U.S. Pat. No. 6,086,612 to Jansen (Adiam Medizintechnik GmbH & Co. KG, Germany) which discloses a mitral valve prosthesis having a support housing with a large base ring (12) that bears two stays (18, 19) which substantially extend in the ring axis direction and are connected by curved walls for securing two flexible cusps (leaflets). The free ends of the stays form an inner support for the cusps. The base-ring has in the top view a closed, non-round shape with a common longitudinal axis (15) but two transverse half-axes (16, 17) of different sizes. The valve is symmetric about the combined transverse half-axes. The stays lie on the longitudinal axis and form the transition between the two halves of the valve. The less curved wall (13) carries a mural cusp having a smaller surface and a higher angle of inclination relative to the base ring base surface than the leaflet connected to the more curved wall (14). The material for the cusps (leaflets) can be synthetic resin foils known from the state of the art, preferably thermoplastic elastomers or synthetic resins with elastomeric properties such as a flexible polyurethane foil.

Another flexible leaflet valve configuration is disclosed in U.S. Pat. No. 6,171,335 to Wheatley, et al. (Aortech Europe Limited, Great Britain). This valve includes a generally annular frame with three posts and three scallops. The frame is tri-symmetric with an axis of symmetry defined by the axis of blood flow through the valve. Each leaflet has a truncated spherical surface adjacent to its free edge that is joined tangentially to a truncated conical surface. The leaflet surface is axi-symmetrical with the axis of symmetry being perpendicular to the axis of the valve frame and blood flow. The leaflets can comprise any biostable, biocompatible thermoplastic elastomer including but not limited to any polyurethane or silicone elastomer or any copolymer or blend based on these elements.

U.S. Pat. No. 6,613,086 to Moe, et al. (CarboMedics Inc., Austin, Tex.) discloses a tri-leaflet prosthetic cardiac valve with leaflets having an analytic shape in a selected position. The leaflets are connected to a valve body at attachment curves. The shape of the leaflet is selected from a set of geometries that can be represented mathematically. The attachment curve is selected to improve the durability of the tri-leaflet valve by moving the point of maximum loaded stress along the attachment curve away from the commissures. An inner wall of the valve body is given a non-circular shape near the attachment curve, the shape of the inner wall corresponding to the attachment curve.

Unfortunately, some proposed valves deteriorate quickly, and some inordinately restrict flow which undesirably reduces the amount of oxygen supplied to the body. The manufacturing process of tissue heart valves is very mature and complex from the quality control point of view, and only minimal improvements in valve durability have been achieved in recent years. Accordingly, despite much development work on heart valves in the past three decades, there remains a need for a more durable valve that permits more blood to flow.

SUMMARY OF THE INVENTION

The present invention provides a next-generation prosthetic heart valve having flexible leaflets that more closely approximates the actual shape of a natural mitral valve. The prosthetic heart valve desirably includes an asymmetric base periphery and three flexible leaflets. Because of the asymmetry, one of the leaflets is larger than the other two. Simultaneously, the two commissure posts of the base that flank the larger leaflet are taller than the other commissure posts. To help increase orifice valve area, the overall height profile of the valve has been reduced so that the valve may be implanted intra-atrially. Certain aspects of the present invention may be applicable to prosthetic heart valves indicated for implantation in other than the mitral position.

In accordance with one embodiment of the invention, a prosthetic heart valve comprises a base structure having a non-circular central flow orifice oriented around a flow axis, and three flexible leaflets mounted on the base structure and projecting into the flow orifice. Preferably, the non-circular central orifice is elliptical in shape. If the valve is indicated for placement in a mitral annulus, then the non-circular central orifice may be in the shape of a mitral annulus in its systolic phase (often a "D" shape).

The base structure may include a stent having three cusps on an inflow end and three commissures on an outflow end. The three flexible leaflets each include a cusp edge terminating in a pair of commissure edges, with a free edge extending between the commissure edges and opposite the cusp edge. Each leaflet attaches along its cusp and commissure edges to a cusp and two associated commissures of the stent. In one embodiment, the stent includes a wireform having cusps and commissures, and each leaflet commissure edge includes a tab that extends radially outward with respect to a wireform commissure and attaches on the outer side thereof. The stent may further include a primary band having an outflow edge that mimics the alternating cusp and commissure shape of the wireform and is located radially outward from the wireform. The leaflet tabs attach to the band outward from the wireform commissures. In addition, a secondary band surrounding the primary band may be provided to add rigidity to a common inflow edge thereof.

Desirably, at least one of the three flexible leaflets is configured differently than one of the others. For example, one of the three flexible leaflets may be substantially larger than the other two. If the prosthetic heart valve is oriented for placement within the mitral annulus, the larger leaflet is on an anterior side of the valve and the two smaller leaflets are on a posterior side of the valve. In a preferred embodiment, the base structure includes a stent having three cusps on an inflow end and three commissures on an outflow end. The three flexible leaflets each include a cusp edge terminating in a pair of commissure edges, with a free edge extending between the commissure edges and opposite the cusp edge. Each leaflet attaches along its cusp and commissure edges to a cusp and two associated commissures of the stent, and the two commissures of the stent to which the larger leaflet attaches may have greater dimensions along the flow axis than the third commissure.

In accordance with another aspect of the invention, a prosthetic heart valve is provided that has a base structure having a central flow orifice oriented around a flow axis. Three flexible leaflets mount on the base structure and project into the flow orifice, and at least one of the three flexible leaflets is configured substantially differently than at least one of the others. For example, one of the three flexible leaflets is substantially thicker than the other two. Alternatively, or in addition, one of the three flexible leaflets is substantially larger in occluding area than the other two.

If the prosthetic heart valve is oriented for placement within the mitral annulus, the larger leaflet is on an anterior side and the two smaller leaflets are on a posterior side. If the prosthetic heart valve has the aforementioned base structure with a stent having commissures, then the two commissures of the stent to which the larger leaflet attaches have greater dimensions along the flow axis than the third commissure. The central orifice of the valve may be elliptical and define a major axis and a minor axis. Preferably, the minor axis bisects the larger leaflet. In one embodiment, the central orifice is in the shape of a mitral annulus in its systolic phase, with a longer dimension and a shorter dimension in plan view. In the latter embodiment, an axis extending generally along the shorter dimension of the central orifice bisects the larger leaflet.

In accordance with a still further aspect of the invention, a prosthetic heart valve has a plurality of flexible leaflets and a base structure on which the leaflets mount. The base structure has a central flow orifice oriented about a flow axis and includes a stent having a plurality of cusps on an inflow end and the same number of commissures on an outflow end. At least one of the commissures has a different axial dimension than at least one other commissure. The central orifice may be non-circular, for example elliptical. Or, the prosthetic heart valve may be configured for placement in a mitral annulus, wherein the non-circular central orifice is in the shape of a mitral annulus in its systolic phase.

The flexible leaflets each may include a cusp edge terminating in a pair of commissure edges, with a free edge extending between the commissure edges and opposite the cusp edge. The stent desirably includes a wire form having cusps and commissures, wherein each leaflet attaches along its cusp and commissure edges to a cusp and two associated commissures of the stent. Preferably, at least one of the flexible leaflets is configured differently than one of the others. For example, one of the leaflets may be larger in occluding area than the other leaflets. In this embodiment, there are at least two of the commissures of the stent that have greater dimensions along the flow axis than at least one other commissure, wherein the larger flexible leaflet attaches to the two larger stent commissures. If the prosthetic heart valve is oriented for placement within the mitral annulus and has three flexible leaflets, the larger leaflet is positioned on an anterior side and two smaller leaflets are positioned on a posterior side. Preferably, at least one of the commissures has an axial dimension that is less than about 85% than at least one of the other commissure.

The invention also contemplates a prosthetic heart valve having a lower outflow profile, comprising a base structure and a plurality of flexible leaflets mounted thereon. The base structure has a central flow orifice oriented around a flow axis, and the mounted leaflets project into the flow orifice. The leaflets are mounted in the base structure so as to define a leaflet axial dimension from their inflow ends to their outflow ends thereof. The valve also includes a sewing ring mounted around the base structure at an attachment elevation. To provide the low profile, the distance between the attachment elevation and the outflow end of the leaflets relative to the leaflet axial dimension is less than about 75%.

The present invention also provides a prosthetic mitral heart valve suitable for intra-atrial implant. The intra-atrial valve includes a base structure having a central flow orifice oriented around a flow axis, the base structure including a stent having a plurality of cusps on an inflow end and the same number of commissures on an outflow end. A plurality of flexible leaflets mount on the base structure and project into the flow orifice. A sewing ring mounts around the base structure such that none of the commissures of the base structure projects axially in the outflow direction from the attachment line of the sewing ring far enough to contact and injure the interior of the left ventricle. Preferably, the sewing ring has a scalloped inflow profile.

DESCRIPTION OF THE PREFERRED EMBODIMENTS

The present invention pertains to prosthetic heart valves that simulate the natural human heart valve anatomy, in particular for the mitral valve. For instance, the shape of the flow orifice is non-circular so as to mimic the shape of the mitral annulus in the systolic phase. Also, in a preferred embodiment three leaflets are utilized with at least one being substantially different than the other two. The reader will see from the following description and appended drawings various features of the exemplary valves that are intended to mimic the natural mitral valve. However, because of the nature of prosthetic heart valves in terms of durability and implantation requirements, a prosthetic valve cannot precisely mirror a natural valve. Accordingly, the prosthetic mitral valve disclosed herein is termed "anatomically approximate" to indicate one or more modifications from conventional prosthetic valves that render it more like a natural valve. It should be noted that one or more of these features that render the valve "anatomically approximate" may be applicable to prosthetic valves for implantation in other than the mitral position, such as in the aortic position. As such, unless a feature is specifically applicable to the mitral position the invention should not be considered so limited.

Several considerations drive the development of an anatomically approximate heart valve. For instance, in the mitral position the native anatomy comprises a relatively large anterior leaflet extending between the fibrous trigones and a posterior leaflet commonly subdivided into three scalloped shapes. In the systolic phase, the mitral annulus generally assumes an oval or elliptical shape with a short or minor axis approximately bisecting the anterior leaflet, midway between the trigones. Conventional prosthetic heart valves have circular base structures creating a circular orifice, which may not be an optimum shape to facilitate active opening of the leaflets and maximum flow through the orifice. The present invention provides a valve with a base structure that mimics the shape of the mitral annulus in the systolic phase and facilitates active opening of the leaflets and better blood flow. In addition, the more naturally-shaped base structure in conjunction with leaflets that better simulate the native leaflets is believed to reduce stresses imposed on various components of the prosthetic valve because the structure more faithfully simulates the native anatomy. Less stress on the valve may lead to a more durable implant. These and other design considerations were factors in the development of the present invention.

One of the features that makes the present prosthetic heart valve more anatomically approximate is that one flexible leaflet is larger than the other two. Because there are three leaflets, the larger leaflet spans a circumferential angle of more than 120°. Accordingly, the adjacent commissure posts of the base structure are somewhat larger than prosthetic valves of the prior art. In the mitral position, the outflow end of the valve projects toward and into the left ventricle. To compensate for the larger commissure posts which might extend far enough to contact and injure the interior of the left ventricle, the present invention provides an innovative sewing ring in conjunction with the valve base structure such that the valve can be positioned farther into the left atrium. This implant position is termed "intra-atrial placement" because the valve is sewn to the atrial side of the mitral annulus, as opposed to within the annulus (intra-annular). Because of the mitral anatomy at this location, the sewing ring has a scalloped inflow profile which is different than previous annular mitral valve sewing rings. Though it is well-known to provide a scalloped or undulating sewing ring for prosthetic aortic valves, the present application is believed to be the first to incorporate such structure into a mitral valve sewing ring.

For definitional purposes, heart valves of the present invention are of the flexible leaflet type, as opposed to mechanical valves with rigid leaflets or balls for occluding members. The term "flexible leaflet" encompasses bioprosthetic leaflets such as bovine pericardium, leaflets in whole xenograft (e.g., porcine) valves, bioengineered materials, and synthetic leaflets. The flexible leaflets are mounted from a peripheral base structure so as to project inward into a flow orifice defined by the base structure.

The term "base structure" broadly covers structures having wireform, stents, and the like. For example, the exemplary embodiment of the present invention includes an undulating cloth-covered wireform to which peripheral edges of three leaflets are sewn. The term "cloth" as used herein encompasses a variety of biocompatible fabrics, the most commonly used being polyester terephthalate. Additionally, a dual-band structure surrounds the wireform and provides additional support for the leaflets. Another similar base structure is disclosed in U.S. Pat. No. 6,350,282 to Medtronic, Inc. of Minneapolis, Minn. Another base structure disclosed in U.S. Pat. No. 5,824,069 to Medtronic, Inc. has a "stent" as a base structure that supports flexible leaflets. The stent defines an undulating outflow edge, similar to a wireform. It should also be noted that a "wireform" could be made from a variety of materials, including biocompatible metals such as Elgiloy and polymers such as Delrin. Another "base structure" that can be modified to incorporate certain features of the present invention is shown in U.S. Pat. No. 6,610,088 to Gabbay and includes a "stent" with an undulating outflow edge that provides support for flexible leaflets.

Finally, the term "base structure" encompasses conventional heart valve stents/wireforms designed to be delivered during open heart surgery, and also compressible/expandable base structures designed for minimally-invasive surgeries, such as shown in U.S. Pat. No. 5,411,552 to Andersen, et al. The patent to Anderson, et al. also discloses a whole cardiac valve connected to the stent structure which is a variation covered by the term "flexible leaflets."

With reference now to FIGS. 1-4, an exemplary prosthetic heart valve 20 of the present invention is shown in various views. In general, the heart valve 20 includes a plurality of flexible leaflets 22a, 22b, 22c supported by a peripheral base structure 24 and projecting inwardly therefrom toward a central flow axis 26. A suture or sewing ring 28 attaches around the outside of the base structure 24 and provides a platform through which attachment structure may be passed to hold the valve 20 in place within the body. Typically, heart valves are secured within the affected annulus using an array of sutures passed through the sewing ring 28, although staples, clips, and other such devices may alternatively be used.

Figure 2:
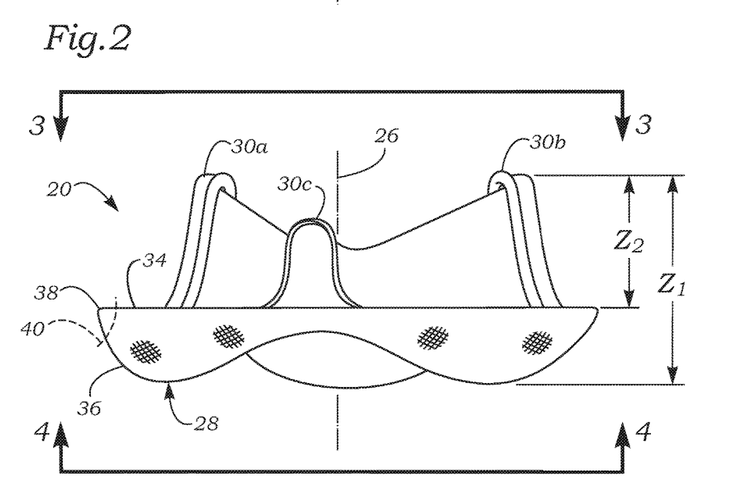

The heart valve 20 includes a plurality of commissures 30a, 30b, 30c, the latter being smaller in axial dimension, as seen in elevation in FIG. 2. The upper tips of the commissures 30a, 30b, 30c define an outflow end of the valve 20 while the lower extremity of the sewing ring 28 defines an inflow end. As will be clear below, each of the leaflets 22a, 22b, 22c includes a peripheral cusp edge that attaches around the base structure 24 between two adjacent commissures 30, a pair of commissure edges on either end of the cusp edge that attach to the two commissures, and a free edge 32a, 32b, 32c (see FIG. 3) that extends across the flow orifice between the two commissures. As with many conventional flexible leaflets valves, the leaflets 22a, 22b, 22c project into the flow orifice toward the axis 26 and meet or "coapt" in a tri-foil configuration. The valve 20 is shown in the figures in its closed state with the leaflets 22a, 22b, 22c coapting together along three lines radiating generally from the flow axis 26.

With reference to FIG. 2, the heart valve 20 has an axial height as indicated at $Z_1$ from the inflow end to the outflow end. As illustrated, the axial height $Z_1$ extends from the lowermost point of the sewing ring 28 to the tip of one of the two larger commissures 30a or 30b. In the exemplary heart valve 20, this axial height $Z_1$ is approximately equal to the axial dimension of the leaflets 22, at least at the two larger commissures 30a, 30b. As will be explained in more detail below, the cusp edge of each of the leaflets mounts to the base structure 24 along a line that is close to the lowermost extent of the sewing ring 28, and extends upward into proximity with the tips of the commissures. Therefore, for purpose of definition in this valve embodiment, the valve axial height $Z_1$ will be deemed analogous to the leaflet axial dimension.

The axial dimension $Z_2$ shown in FIG. 2 indicates the distance between the uppermost surface 34 of the sewing ring 28 to the tip of one of the two larger commissures 30a or 30b. The uppermost surface 34 of the sewing ring 28 can be defined as an attachment elevation for the heart valve 20. That is, the surgeon passes sutures or other devices through both the side surface 36 and the upper surface 34 of the sewing ring 28, essentially forming a loop around the outer periphery or apex 38, as indicated by the dashed line 40. Although there is no single plane of attachment of the sewing ring 28, the upper surface 34 will be termed the attachment elevation for purpose of reference.

The heart valve 20 of the present invention has a relatively low-profile from the sewing ring 28 to the outflow end. More precisely, the dimension $Z_2$ is smaller in proportion to the leaflet axial dimension $Z_1$, in comparison with heart valves of the prior art. An alternative way to see this is that the taller commissures 30a, 30b project in the outflow direction a shorter distance from the sewing ring 28 relative to the valve axial height $Z_1$ in comparison to other prosthetic heart valves, in particular prosthetic mitral valves. Preferably, the distance between the attachment elevation (sewing ring upper surface 34) and the outflow end of the leaflets, relative to the leaflet axial dimension, is less than about 75%. For the mitral position, this construction enables the heart valve 20 to be implanted in the intra-atrial position. That is, the sewing ring 28 attaches to the tissue of the left atrium adjacent to the mitral annulus, rather than directly within the annulus. This low-profile commissure construction helps insure that the tall commissures 30a, 30b do not undesirably project too far into the left ventricle, possibly causing injurious contact with the inner ventricle wall.

The reason that the commissures 30a, 30b are taller than those of conventional heart valves of the same type is that one of the leaflets 22 is configured substantially differently than at least one of the others. Namely, one leaflet 22a is substantially larger in occluding area than the other two leaflets 22b or 22c. This can best be seen in FIGS. 3 and 4, which are plan views from the outflow and inflow ends, respectively.

Figure 3:
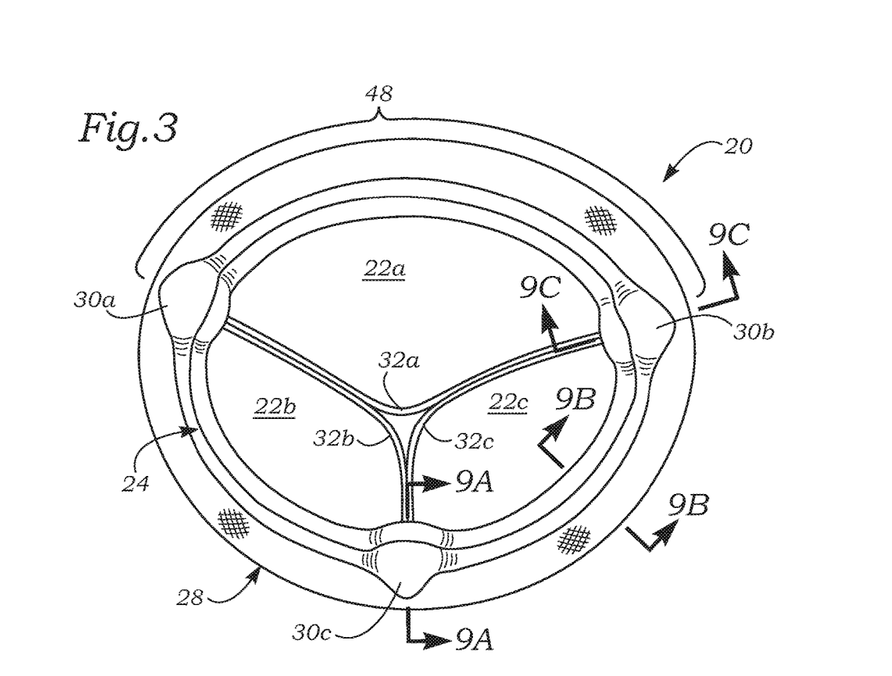
FIGS. 3 and 4 heart topic and bottom plane views, respectively, of the prosthetic mitral heart valve of FIG. 2.

The base structure 24 defines a non-circular flow orifice within which the three leaflets are supported. In the orientation of FIG. 3, the horizontal dimension of the base structure 24 is greater than the vertical dimension, creating somewhat of an elliptical or oval shape. When utilized in the mitral position, the peripheral shape of the base structure 24 is desirably in the shape of the mitral annulus in its systolic phase, which is substantially elliptical or D-shaped. As an approximate rule of thumb, the ratio of the minor axis (vertical) dimension to the major axis (horizontal) dimension is approximately 3:4, although it is believed that a ratio of 5:4 may be more suitable for the exemplary prosthetic mitral valve 20.

Still with reference to FIG. 3, when the heart valve 20 is to be used in the mitral position, the leaflets 22a, 22b, 22c are oriented to approximately mirror the native leaflet orientation and relative sizes. That is, that the first leaflet 22a extends between first and second commissures 30a, 30b that are spaced apart around the circumference of the valve 20 at the approximate location of the fibrous trigones of the mitral annulus. Therefore, the first leaflet 22a simulates the anterior leaflet of the mitral annulus, and the upper portion 48 of the valve 20 as shown in FIG. 3 represents an anterior aspect thereof. Conversely, the lower portion (not numbered) of the valve 20 as shown in FIG. 3, between the first and second commissures 30a, 30b, represents a posterior aspect. Of course, the valve 20 must be implanted in this orientation to obtain the intended benefits.

Figure 4:
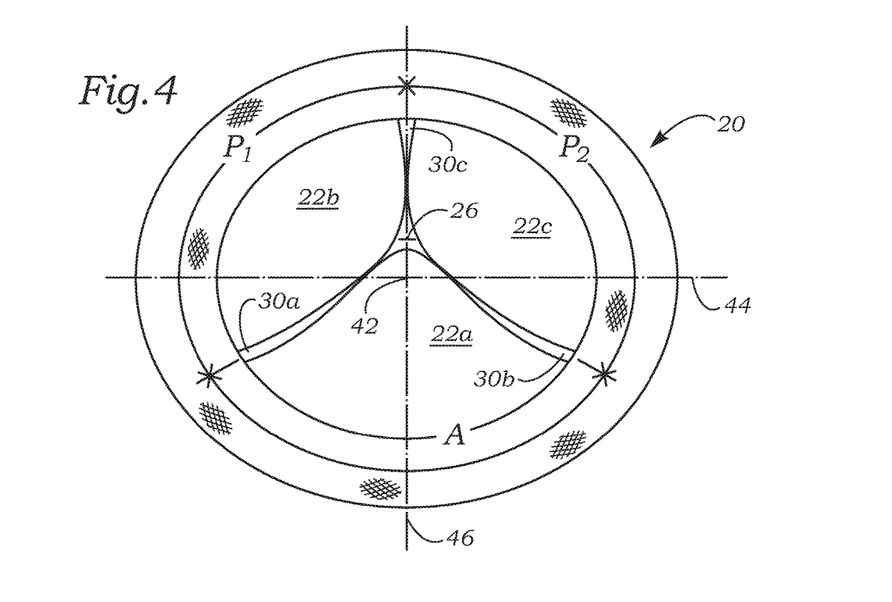

As indicated in FIG. 4, the angular distance A around the anterior aspect of the base structure 24 between the first and second commissures 30a, 30b is substantially greater than the angular distance $P_1$ from the first commissure 30a to the third commissure 30c, or the angular distance $P_2$ from the second commissure 30b to the third commissure 30c. The sum of the angular distances $P_1$ and $P_2$ represents the posterior aspect of the valve 20. In a preferred embodiment, the angular distance A is between about 34-40%, and more preferably approximately 35% (125°), of the total angular distance around the valve periphery.

Because the first and second commissures 30a, 30b are spaced farther apart than any other pair of commissures, the first leaflet 22a is substantially larger than the second and third leaflets 22b, 22c. Indeed, because the angular span of the first leaflet 22a is greater than 120°, the heights of the first and second commissures 30a, 30b must be taller than the third commissure 30c (and taller than commissures of prior art valves) to ensure that the three leaflets meet at the same elevation in the middle of the flow orifice. Also, it should be noted that the first leaflet 22a is desirably symmetric about a plane bisecting the leaflet between the first and second commissures 30a, 30b, but the second and third leaflets 22b, 22c may not be likewise symmetric because they attach to commissures of unequal heights. The specific shape of the three leaflets will be described below with reference to FIGS. 10A and 10B.

In one exemplary embodiment of the invention, existing prosthetic heart valve leaflets may be used to construct the anatomically approximate heart valve 20. In general terms, heart valves are labeled by the diameter of their orifice, typically between 25 millimeters and 33 mm in odd increments (i.e., 25-27-29-31-33), which provides an adequate selection of sizes for most patients. For definitional purposes, a 29 mm heart valve 20 of the present invention has a nominal major axis dimension of 29 mm. The exemplary heart valve 20 may have a larger leaflet 22a that is otherwise conventional but sized for use in a larger heart valve of the prior art (i.e., circular), while the smaller leaflets 22b, 22c may be indicated for use in a smaller heart valve of the prior art. For example, a 29 mm heart valve 20 of the present invention may utilize a single larger leaflet 22a that would otherwise be suitable for use in a conventional 33 mm prosthetic valve, while the two smaller leaflets 22a, 22b are sized for use in a conventional 27 mm prosthetic valve. Another way to state this is that the larger (anterior) leaflet 22a is preferably two sizes above the nominal size of the valve (e.g., 33 mm leaflet for a 29 mm valve), while the smaller (posterior) leaflets 22a, 22b are one size below (e.g., 27 mm leaflets for a 29 mm valve).

FIG. 4 also illustrates an offset between the approximate flow axis 26 (approximate because the leaflets are flexible and the precise center of the flow axis may vary) and the geometric center 42 of the valve 20. The geometric center 42 lies at the intersection of a major axis 44 and a minor axis 46 of the generally elliptical valve 20. The offset stems from the uneven nature of the three coapting leaflets 22a, 22b, 22c.

With reference again to FIG. 3, a preferred difference in the thickness of the leaflets is shown. The free edge 32a of the first leaflet 22a is illustrated slightly thicker than the free edges 32b, 32c of the second and third leaflets 22b, 22c. Because of the larger area of the first leaflet 22a, it will be subjected to a greater overall force from the pressure of the blood flow when the valve closes (the systolic phase of the mitral valve). Therefore, at least for bioprosthetic tissue such as bovine pericardium, it is desirable that the larger leaflet 22a be made somewhat more robust than the other two leaflets to have a comparable usable life (i.e., durability). In one embodiment, the thickness of the larger leaflet 22a is between about 10-100% greater than the thickness of the other two leaflets.

In accordance with an exemplary fabrication method, the leaflet selection methodology disclosed in U.S. Pat. No. 6,245,105 (expressly incorporated herein) may be used to provide stronger tissue for the larger leaflet 22a than for the other leaflets. The selection methodology utilizes one or more tests, for example a deflection test, to determine the relative elasticity or stiffness of each leaflet. Because of the non-uniform nature of certain bioprosthetic tissue, for example bovine pericardium, the same size leaflets cut from different portions of tissue may have different mechanical properties. In accordance with an exemplary fabrication method, relatively stronger (e.g., stiffer) leaflets are selected for use as the larger leaflet 22a, but relatively softer membrane-like leaflets are used as the smaller leaflets 22b, 22c. It should be noted that these characteristics can generally be predicted merely from measuring the thickness of the tissue, but the supplemental selection methodology disclosed in U.S. Pat. No. 6,245,105 is desirably used to further distinguish between leaflets of the same thickness.

Wireform or Stent

Figure 5A:
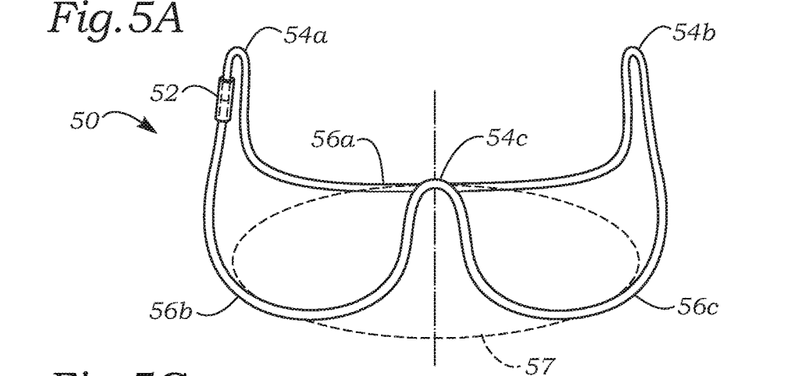
FIGS. 5A-5C are perspective, plan, and elevational views, respectively, of a wireform or stent forming a part of a base structure of an exemplary prosthetic mitral heart valve of the present invention.
Figure 5B:
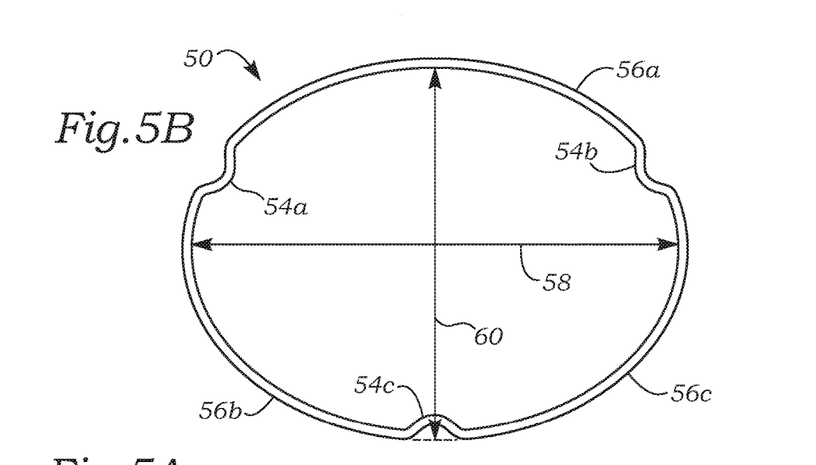
Figure 5C:
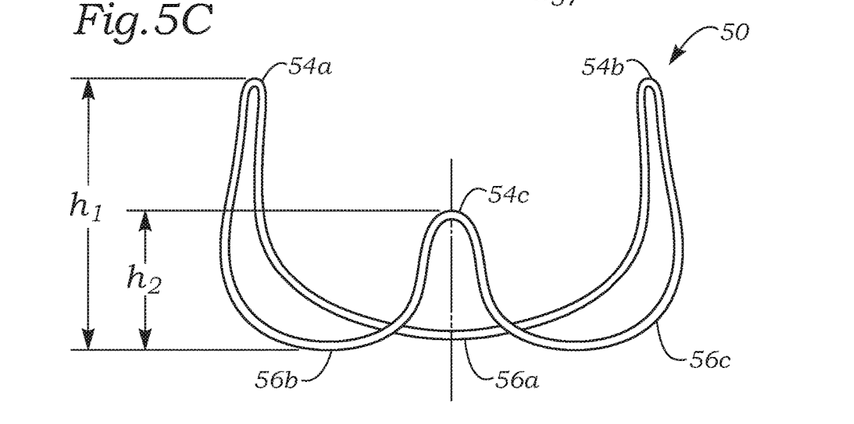

FIGS. 5A-5C illustrate an exemplary wireform 50 that forms a part of the valve base structure 24. In a preferred embodiment, the wireform 50 comprises a wire-like metal alloy such as Elgiloy that may be formed a number of ways. A conventional forming method is to bend a straight wire into the three-dimensional shape and join the two free ends with a crimp 52 as seen in FIG. 5A. Alternatively, a specially-shaped blank may be separated from a sheet or tube of material and then bent into shape using heat treating, for example. In the latter method, the wireform 50 starts out as a continuous closed blank, and therefore there is no need for the crimp 52, as in FIGS. 5B and 5C. Furthermore, if the wireform 50 is made of a polymer it can be molded directly into the continuous closed shape shown.

The wireform 50 comprises alternating commissures 54a, 54b, 54c on the outflow end and cusps 56a, 56b, 56c on the inflow end. The commissures 54 (sometimes termed posts) comprise relatively narrow converging straight portions, terminating in arcuate tips with relatively small radii. The cusps 56, in contrast, are continuously curved and have relatively large radii. As seen in the plan view of FIG. 5B (and by the dashed line 57 connecting the cusp 56 midpoints in FIG. 5A) the peripheral shape of the wireform 50 is generally elliptical with a major axis 58 and a minor axis 60. The relative orientation of the three commissures 54 is seen again in FIG. 5B, with the first and second commissures 54a, 54b being spaced apart an angular distance of greater than 120°. The commissures 54 desirably angle slightly radially inwardly from the adjacent cusps 56 so that the wireform 50 defines an approximately conical shape.

In the exemplary construction of heart valve 20, the peripheral edges of the leaflets attach to the wireform 50, and therefore the wireform (sometimes termed the "stent") defines the shape of the flow orifice and the three-dimensional support structure for the leaflets. The contour of the wireform 50 (or stent) thus defines the leaflet axial dimension. It is worth repeating here that the heart valve 20 preferably has a sewing ring attachment line that is closer to the outflow end of the valve relative to the leaflet axial dimension (stent height) as compared with valves of the prior art. As stated above, other valve constructions may not utilize a wireform, but the same principles apply with respect to the low-profile sewing ring, albeit relative to wherever the leaflets attach.

The total axial height $h_1$ of the wireform 50 is indicated in FIG. 5C and extends from a plane in which lie the three cusps 56a, 56b, 56c to the tips of the equally sized first and second commissures 54a, 54b. The axial height $h_2$ of the third commissure 54c is less than $h_1$, preferably less than about 85% of $h_1$. Because the three commissures 54 perform essentially the same function, that of resiliently supporting the commissure edges of two adjacent leaflets, they are similarly shaped if not equally sized.

The commissure heights of the exemplary wireform 50 may be compared with the heights of the commissures of conventional valves to provide a level of context. For an exemplary heart valve 20 of the present invention labeled for use in a 29 mm annulus, the axial height $h_2$ of the third commissure 54c is desirably about 3 mm less than the height of a commissure of a conventional 29 mm prosthetic heart valve. From the same valve, the axial height $h_1$ of the first and second commissures 54a, 54b is desirably about 1 mm less than the height of a commissure of a conventional 29 mm prosthetic heart valve. It should be noted that these relative dimensions are derived by comparing an exemplary 29 mm mitral heart valve 20 of the present invention with a 29 mm prosthetic mitral heart valve sold under the trade name Carpentier-Edwards PERIMOUNT Pericardial Bioprosthesis by Edwards Lifesciences of Irvine, Calif.

Support Bands

Figure 6A:
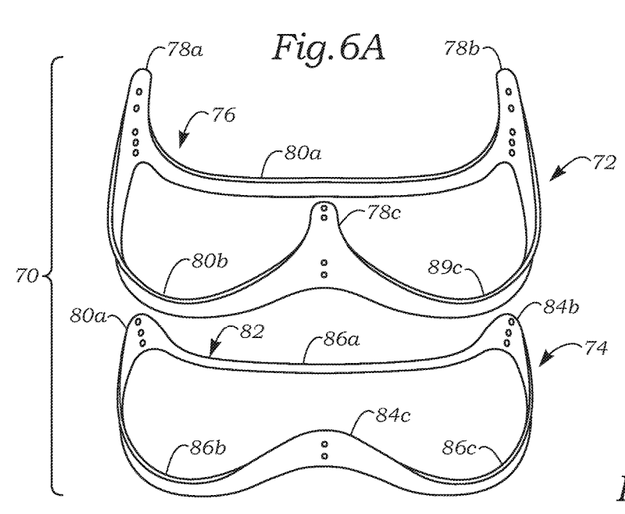
FIGS. 6A and 6B are perspective exploded and assembled views of a support band combination forming a part of the base structure of an exemplary prosthetic mitral heart valve of the present invention.
Figure 6B:
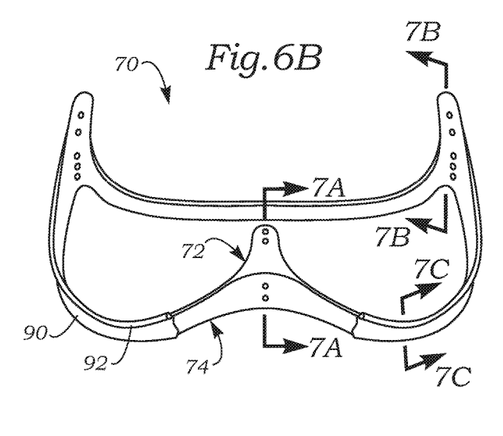

FIGS. 6A and 6B illustrate, respectively, exploded and assembled views of a support band combination 70 that forms a part of the valve base structure 24. The support band combination includes a primary band 72 and a secondary band 74 surrounding the primary band. The primary band 72 defines a closed shape similar to the wireform 50 described above, and includes an outflow edge 76 with alternating commissure sections 78a, 78b, 78c and cusp sections 80a, 80b, 80c. The secondary band 74 also defines a closed shape similar to the primary band, and has an outflow edge 82 with commissure sections 84a, 84b, 84c and cusps sections 86a, 86b, 86c. The outflow edge 76 of the primary band 72 is shaped to closely follow the contours of the wireform 50. As such, the first and second commissure sections 78a, 78b are taller than the third commissure section 78c. Although the commissure sections 84 of the secondary band outflow edge 82 are truncated with respect to those of the primary band 72, the first and second sections 84a, 84b are taller than the third section 84c. These different heights are seen best in FIGS. 7A and 7B.

Figure 7A:
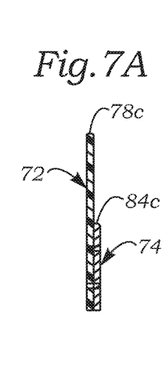
FIGS. 7A-7C are cross-sectional views of the assembled support band combination taken along the indicated section lines in FIG. 6B.
Figure 7B:
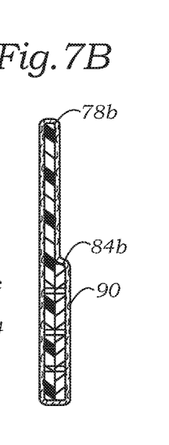
Figure 7C:
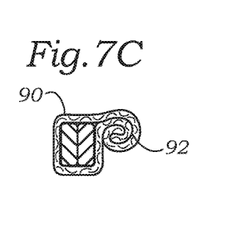

As seen by the assembled view of FIG. 6B, and the cross-sections of FIGS. 7A-7C, the secondary band 74 closely surrounds and is coupled to the primary band 72. Although not numbered, the inflow edges of the two bands 72, 74 coincide to form a single common inflow edge in the assembled combination. FIG. 6B illustrates in partial cutaway a cloth covering 90 encompassing the combination. The cloth covering 90 is rolled into a cuff 92 that extends outward from the two bands along the cusp sections 80, 86, and partially up the commissure sections 78, 84. The cuff 92 is seen in cross-section in FIG. 7C and provides a sewing rim facilitating assembly of the valve, as will be described below. The two bands 72, 74 include a number of radial holes through which coupling sutures (not shown) can be passed for joining the two bands together, and for securing the cloth covering to the combination.

In a preferred embodiment, the primary band 72 is formed of a material that is relatively more flexible than the secondary band 74. As will become clearer below, the flexible leaflets of the valve attach to the uppermost portions of the commissures of the flexible primary band 72, which does not inhibit flexing of the valve commissures during the systolic, or valve closing, phase. Conversely, the more rigid secondary band 74 provides stability to the basic structure around the inflow edge and cusps. For example, the primary band 72 may be formed of a polymer such as Delrin while the secondary band 74 is form of a metallic alloy such as Elgiloy.

Exemplary Low-Profile Sewing Ring

As mentioned previously, the preferred use for the anatomically approximate prosthetic heart valve 20 is in the mitral annulus. Because of the large anterior leaflet and taller commissures, the valve 20 desirably seats farther into the left atrium than prior art mitral heart valves to help prevent contact of the commissures with the interior of the left ventricle. This implant position is termed intra-atrial because the sewing ring is positioned on the atrial side of the mitral annulus, rather than within the annulus. To accomplish this, the aforementioned sewing ring 28 is wider in the radial direction and attaches to the base structure 24 relatively closer to the outflow end of the valve in comparison with conventional valves.

Figure 1:
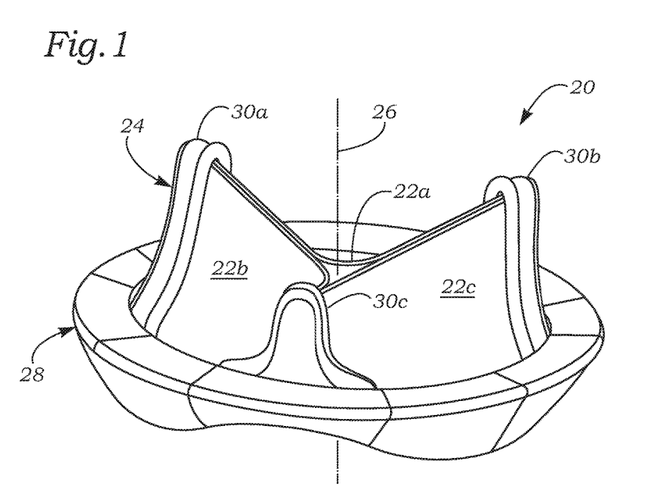
FIGS. 1 and 2 are perspective and elevational views, respectively, of an anatomically approximate prosthetic mitral heart valve of the present invention.
Figure 8A:
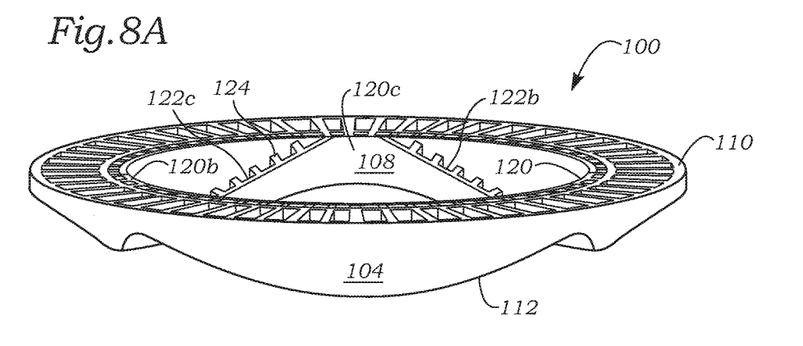
FIGS. 8A and 8B are perspective and top plan views, respectively, of an exemplary sewing ring sponge used in conjunction with the exemplary valve base structure to create a low-profile heart valve and therefore enable intra-atrial placement in the mitral position.
Figure 8B:
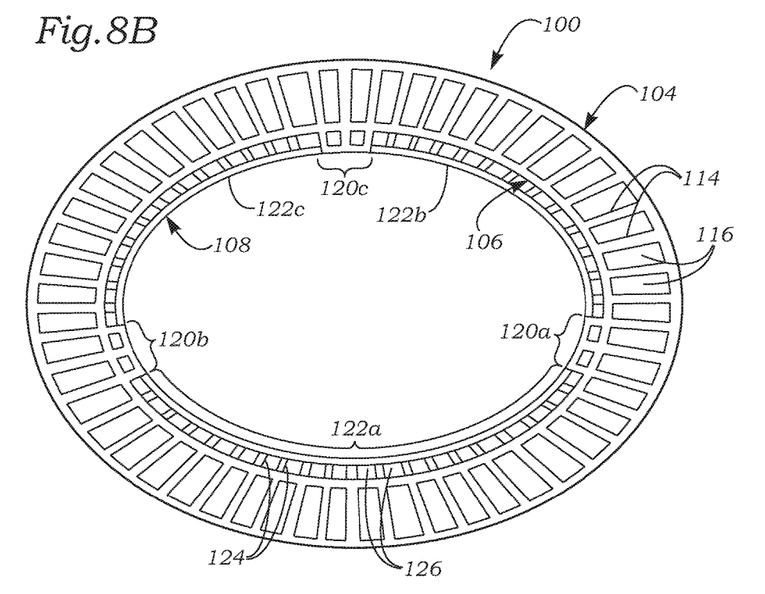

FIGS. 8A and 8B are two views of an exemplary sewing ring sponge 100 that makes up the primary component of the sewing ring 28 shown in FIG. 1. That is, the sewing ring 28 comprises the sponge 100 with a cloth covering 102, seen in FIGS. 9A-9C. It should be understood that though the sewing ring sponge 100 is desirably a molded silicone rubber element, other materials and fabrication techniques may be used to form a suture-permeable, contoured sewing ring. For purpose of orientation, the outflow direction of the valve is up in FIG. 8A.

The sponge 100 comprises a plurality of walls of approximately equal thickness defining multiple opens cells therebetween. With reference to FIG. 8B, the sponge 100 includes an outer wall 104, an intermediate wall 106 spaced inwardly from outer wall, and an inner wall 108 that defines the innermost surface of the sponge. The elliptical outflow rim 110 of the outer wall 104 extends in a plane and defines the outermost extent of the sponge 100. The outer wall 104 includes a short axial segment on the outflow end, but curves inward toward the inflow end and terminates in a scalloped inflow edge 112. The inflow edge 112 defines an undulating shape that generally mirrors the up and down contours of the wireform 50 of the valve. The intermediate wall 106 is oriented substantially axially and in the elliptical shape of the outflow rim 110. A plurality of generally radially oriented cell walls 114 extends between and joins the outer wall 104 and intermediate wall 106, creating a plurality of voids or cells 116.

The inner wall 108 has an undulating configuration as seen best in FIG. 8A, with three elevated segments 120a, 120b, 120c located at the commissures of the valve and three gently downwardly curved segments 122a, 122b, 122c therebetween. A plurality of generally radially oriented cell walls 124 extends between and joins the intermediate wall 106 and inner wall 108 and defines a plurality of voids or cells 126. Just inward from the axial intermediate wall 106, the outflow edges of the downwardly curved segments 122 define three arcuate ledges or depressions on which are supported the three cusps of the base structure 24.

Figures 9A, 9B:
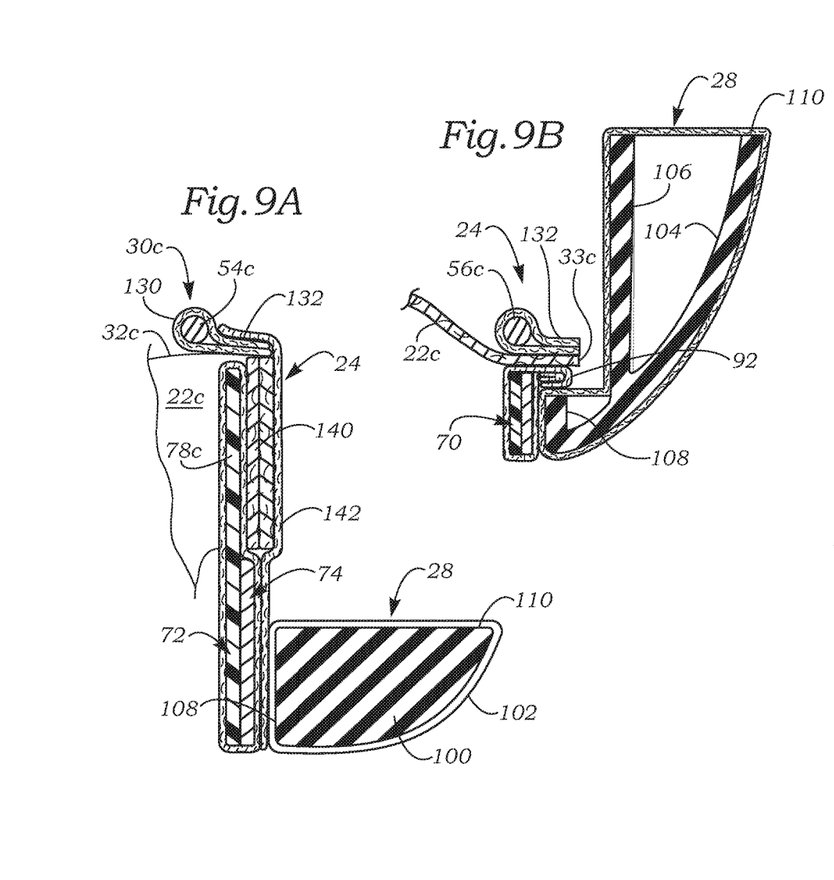
FIGS. 9A-9C are cross-sectional views of the assembled prosthetic mitral heart valve taken along the indicated section lines in FIG. 3.

With reference to FIG. 8B, the first and second elevated segments 120a, 120b of the inner wall 108 correspond to the location of the first and second commissures 30a, 30b of the base structure 24, as seen in FIG. 1. The third elevated segment 120c corresponds to the location of the third commissure 30c. FIG. 8B illustrates the non-symmetric positioning of the three elevated segments 120a, 120b, 120c corresponding to the same positions of the valve commissures. Likewise, the three downwardly curved segments 122a, 122b, 122c correspond to the location of the three wireform cusps 56a, 56b, 56c, seen in FIG. 5A. The curvature of the outflow edges of the segments 122 matches the respective curvatures of the wireform cusps 56 such that the base structure 24 fits closely within the intermediate wall 106 of the sponge 100 and a portion thereof is supported by the ledges created by the undulating inner wall 108. This beneficial construction is shown in FIG. 9B, and described below.

It is the depth of the three downwardly curved segments 122a, 122b, 122c from the outflow rim 110 that provides the "low-profile" characteristic of present valve 20. That is, the cusps of the base structure 24 seat within the sewing ring 28 farther from the outflow rim 110 than in previous valves. Desirably, the axial depth of the midpoint of the segments 122 from the outflow rim 110 is greater than about 80% of the overall axial dimension of the sponge 100. At the same time, the scalloped inflow edge 112 provides a contour that matches the typical anatomical contour of the left atrium adjacent to the mitral annulus. Because the sewing ring 28 attaches farther into the left atrium, this contour reduces interference with the natural movement of the atrium. Stated another way, the contour of the inflow edge 112 is designed to follow the undulating fibrous "skeleton" of the mitral annulus on the atrial side.

Valve Construction

Figure 9C:
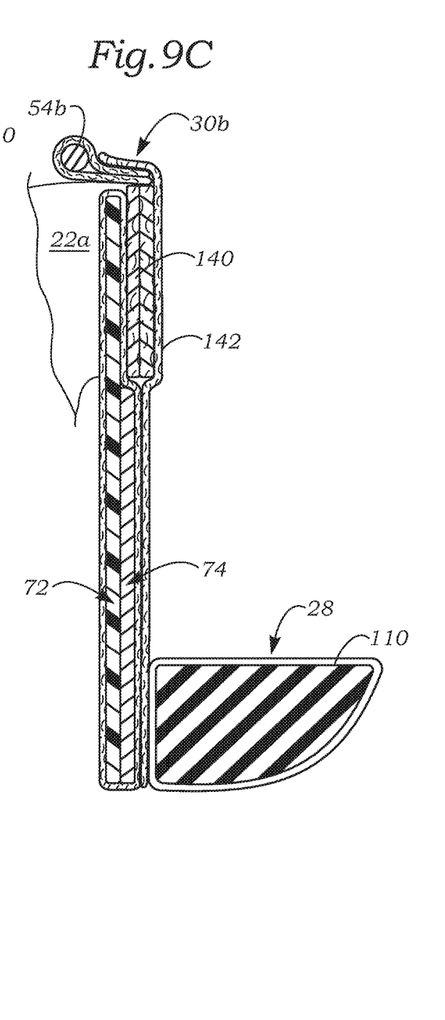

Now with reference to FIGS. 9A-9C certain details with regard to assembly of the various aforementioned components will be explained. FIGS. 9A-9C are taken along the section lines indicated in FIG. 3 at the locations of, respectively, the smaller valve commissure, a midpoint of a valve cusp, and a larger valve commissure. The three cross-sections are shown across the page, with the two commissure views at their relative axial elevations because the outflow rim 110 of the sewing ring sponge 100 remains planar around the periphery of the valve.

FIG. 9A shows the smaller valve commissure with the section line passing through a solid radial wall portion of the sewing ring sponge 100. The cloth covering 102 around the sponge 100 is seen here. The base structure 24 sits within the sewing ring 28 at the commissures. More particularly, the base structure at the small valve commissure 30c includes the smaller commissure sections of the primary band 72 and secondary band 74 positioned slightly radially outwardly from the smaller commissure 54c of the wireform 50. The cloth-covered support band combination 70 is sized to fit closely within the cloth-covered inner wall 108 of the sewing ring 28.

As seen at the top of FIG. 9A, the wireform is enclosed within a cloth covering 130 having two free ends that are joined together to form a cloth flange 132. Although not shown, the cloth covering 130 and flange 132 extend the entire way around the wireform 50 and provide a platform through which sutures may be passed to connect the wireform to the other components of the valve. More particularly, sutures connect the flange 132 to the flexible leaflets 22 (one of which, 22c, is visible) and to the cloth-covered primary support band 72. It should be noted at this point that the various sutures used to assemble components of the valve are not shown in the drawings for clarity.

The flexible leaflets 22 (shown in plan view in FIGS. 10A and 10B) each include a pair of tabs 140 on either side of the free edge 32. Desirably, the tabs extend outward between the converging segments of the wireform commissures 54 and wrap around the respective commissure section 78c of the primary band 72. The tabs are attached with sutures on the outside of the primary band 72 and a further cloth patch 142 may be added to encompass the commissure structure. Connecting the leaflet tabs 140 to the base structure 24 in this manner greatly reduces stresses imposed on the attachment sutures. Because systolic forces on the leaflets are greatest at the commissure tips, it follows that forces on the attachment sutures may also be concentrated at this location. By attaching the tabs 140 on the outside of the primary band 72, the stresses are diffused through the support band and also by the wireform commissure 54. This construction is shown and described in U.S. Pat. No. 5,928,281 to Huynh, et al., the disclosure of which is hereby expressly incorporated by reference.

FIG. 9B is a section through a valve cusp, and illustrates the various walls of the sewing ring sponge 100. Namely, the outer wall 104 has an arcuate shape that extends substantially below its location at the commissure (FIG. 9A), the vertical intermediate wall 106 is dimensioned to receive the valve base structure 24, and the inner wall 108 at its lowest point defines a ledge on which a portion of the base structure seats. The base structure 24 at the cusps include the cusp sections of the support band combination 70, a wireform cusp 56c, and the associated cloth coverings. Again, the cloth-covered support band combination 70 fits closely within the cloth-covered inner wall 108 of the sewing ring 28.

Particular attention is directed to the cloth flange 132 extending outwardly from the wireform which, along with the sewing rim or cuff 92 of the support band combination 70 sandwiches a cusp edge 33c of the leaflet 22c. A line of attachment sutures (not shown) extends around the valve cusps in this manner to provide a continuous, undulating support of the leaflets by the base structure 24. Preferably, the wireform/leaflets/support band subassembly is formed prior to joining with the sewing ring 28. Again, the various attachment sutures are not shown for clarity.

Finally, FIG. 9C is a section through the taller valve commissure, and again shows the sewing ring 28 having the same configuration as at the smaller commissure in FIG. 9A. The taller commissure 30b of the base structure includes the taller commissure sections of the primary band 72 and secondary band 74 positioned slightly radially outwardly from one of the taller commissures 54b of the wireform 50. A portion of the larger leaflet 22a is seen, which also attaches to the base structure in the same manner as described above with respect to the smaller commissure.

Leaflet Configurations

Figure 10A:
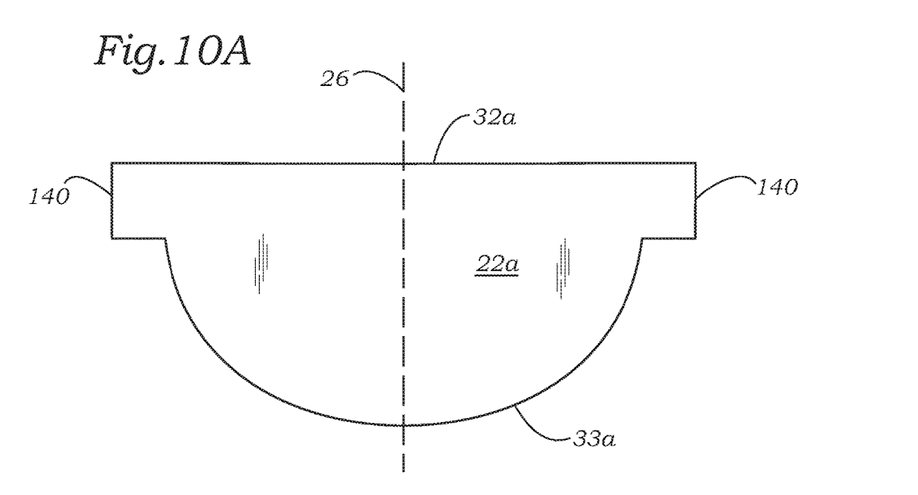
FIGS. 10A and 10B are plan views of two dissimilar flexible leaflets utilized in the prosthetic heart valve of the present invention.
Figure 10B:
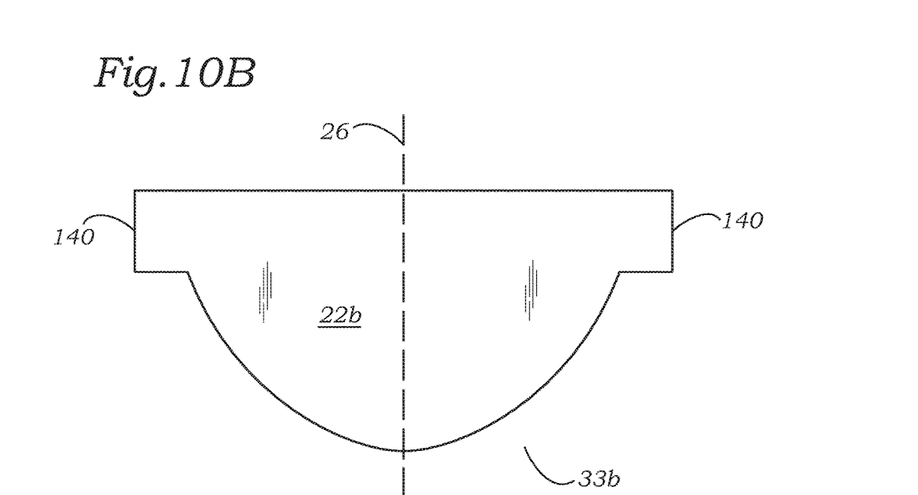

FIG. 10A is a plan view of the larger leaflet 22a showing the aforementioned free edge 32a terminating on the both sides with tabs 140. The arcuate lower cusp edge 33a extends between the tabs 140 opposite the free edge 32a. Because the leaflet 22a is supported at adjacent identical commissures, it is symmetric about a mid-plane passing through the flow axis 26. On the other hand, FIG. 10B shows one of the smaller leaflets 22b which may not be symmetric about the flow axis 26. More area of the smaller leaflets 22b may extend from the flow axis 26 to the larger commissure than to the smaller commissure to which it attaches. Of course, as indicated above, conventional leaflets having different sizes may be utilized which, in plan view, are generally symmetric about a vertical plane through their cusps, but which fold inward within the valve so as to lie slightly asymmetrically because of the shape of the exemplary valve and location of the resulting flow axis.

It will be appreciated that the invention has been described hereabove with reference to certain examples or preferred embodiments as shown in the drawings. Various additions, deletions, changes and alterations may be made to the above-described embodiments and examples, and it is intended that all such additions, deletions, changes and alterations be included within the scope of the following claims.

What is claimed is:

1. A prosthetic mitral valve comprising:
an inflow end, an outflow end, and a central flow axis extending from the inflow end to the outflow end;
a cloth-covered ring disposed at the inflow end of the prosthetic mitral valve, the ring comprising a plurality of cells, an inflow edge of the ring contoured to match a contour of a left atrium adjacent to a native mitral annulus, the ring configured for positioning on an atrial side of the native mitral valve annulus and for holding the prosthetic mitral valve in place;
a compressible and expandable base structure extending from the ring towards the outflow end of the prosthetic mitral valve, the base structure when expanded, being circumferentially D-shaped with a major axis longer than a minor axis thereof, the base structure dimensioned for placement within the native mitral valve annulus, the base structure having a larger diameter towards the inflow end of the prosthetic mitral valve and a smaller diameter towards the outflow end of the prosthetic mitral valve, the base structure comprising a stent including three commissure regions and three cusp regions, the cusp regions of the stent extending towards the inflow end of the prosthetic mitral valve past an outflow portion of the cloth-covered ring;
a cloth cover disposed over the base structure; and
three flexible tissue leaflets in a tri-foil configuration, the leaflets projecting towards the flow axis, the leaflets secured to the stent along the cusp and commissure regions thereof.

2. The prosthetic mitral valve of claim 1, wherein the cloth covering the ring is polyethylene terephthalate.

3. The prosthetic mitral valve of claim 1, wherein the inflow edge of the ring is scalloped.

4. The prosthetic mitral valve of claim 1, wherein the cloth disposed over the base structure is polyethylene terephthalate.

5. The prosthetic mitral valve of claim 1, wherein the tissue leaflets are bovine pericardium.

6. A prosthetic mitral valve comprising:
an inflow end, an outflow end, and a central flow axis extending from the inflow end to the outflow end;
a ring disposed at the inflow end of the prosthetic mitral valve, the ring configured for positioning on an atrial side of a native mitral valve annulus and for holding the prosthetic mitral valve in place;
a compressible and expandable base structure extending from the ring towards the outflow end of the prosthetic mitral valve, the base structure when expanded, being circumferentially oval, elliptical, or D-shaped with a major axis longer than a minor axis thereof, the base structure dimensioned for placement within the native mitral valve annulus, the base structure having a larger diameter towards the inflow end of the prosthetic mitral valve and a smaller diameter towards the outflow end of the prosthetic mitral valve, the base structure comprising a stent including three commissure regions and three cusp regions, the cusp regions of the stent extending towards the inflow end of the prosthetic mitral valve past an outflow portion of the cloth-covered ring; and
three flexible leaflets in a tri-foil configuration, the leaflets projecting towards the flow axis, the leaflets secured to the stent along the cusp and commissure regions thereof.

7. The prosthetic mitral valve of claim 6, wherein the ring further comprises a cover comprising cloth, biocompatible fabric, or polyester terephthalate.

8. The prosthetic mitral valve of claim 6, wherein the ring comprises a plurality of cells.

9. The prosthetic mitral valve of claim 6, wherein an inflow edge of the ring is contoured to match a contour of a left atrium adjacent to the native mitral annulus.

10. The prosthetic mitral valve of claim 9, wherein the inflow edge of the ring is scalloped.

11. The prosthetic mitral valve of claim 6, wherein the base structure is circumferentially D-shaped.

12. The prosthetic mitral valve of claim 6, wherein a ratio of the minor axis to the major axis of the stent is from about 3:4 to about 4:5.

13. The prosthetic mitral valve of claim 6, wherein the commissure regions comprise first and second commissure posts disposed substantially symmetrically about the minor axis, and a third commissure post disposed substantially on the minor axis.

14. The prosthetic mitral valve of claim 6, wherein the commissure regions comprises three commissure posts.

15. The prosthetic mitral valve of claim 6, wherein the commissure regions comprises commissure posts angled radially inwards towards the flow axis.

16. The prosthetic mitral valve of claim 6, further comprising a cover disposed over the base structure.

17. The prosthetic mitral valve of claim 16, wherein the cover comprises at least one of cloth, biocompatible fabric, and polyester terephthalate.

18. The prosthetic mitral valve of claim 6, wherein the tissue leaflets are bovine pericardium.

* * * * *